United States Patent [19]
Shibata et al.

[11] Patent Number: 6,117,913
[45] Date of Patent: *Sep. 12, 2000

[54] INTESTINAL JUICE LEVEL REGULATOR

[75] Inventors: Akira Shibata; Takashi Shibata, both of Osaka; Tomoo Kuge, Hyogo; Norio Ogata, Osaka; Koji Ataka, Wakayama, all of Japan

[73] Assignee: Taiko Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/879,072

[22] Filed: Jun. 19, 1997

[30] Foreign Application Priority Data

Jul. 1, 1996 [JP] Japan .................................. 8-171362

[51] Int. Cl.[7] ............................ A61K 35/04; A61K 31/05
[52] U.S. Cl. ...................... 514/731; 424/195.1; 514/867
[58] Field of Search ................................ 514/731, 867; 424/195.1

[56] References Cited

U.S. PATENT DOCUMENTS

| 3,171,781 | 3/1965 | Lobel | 424/195.1 |
| 4,203,985 | 5/1980 | Yelnosky et al. | 424/249 |
| 4,608,258 | 8/1986 | Yamanaka | 424/195.1 |

FOREIGN PATENT DOCUMENTS

| 0 055 313 | 7/1982 | European Pat. Off. |
| 0 400 219 | 12/1990 | European Pat. Off. |

OTHER PUBLICATIONS

"Pathology", H. Itoh, 6th revised edition, Keiko–do publishers, Jan. 1983.

"The United States Dispsensatory", Osol et al, 27th edition, J.B. Lippincolt Company publishers, Aug. 1981.

Ataka et al, "Suppression of Enterotoxin–Induced Intestinal Fluid Secretion by Wood Creosote", Res Commun Mol Pathol Pharmacol, 93(2), pp. 219–214, Aug. 1996.

Ogata et al, Demonstration of Antidiarrheal and Antimotility Effects of Wood Creosote, Pharmacology, vol. 46, pp. 173–180, Mar. 1993.

Database WPI, Week 915, AN 94–121169, Mar. 1994.

Patent Abstracts of Japan, vol. 12, nol. 37 (C–473) Mar. 1994.

Jacewicz et al, "Textbook of Secretory Diarrehea", Raven Press Ltd, Jan. 1990.

Database Medline, vol. 87, No. 11, pp. 1426–1431, abstract XP002044898, Dec. 1986.

*Primary Examiner*—Frederick Krass
*Attorney, Agent, or Firm*—Jordan and Hamburg LLP

[57] ABSTRACT

An intestinal juice level regulator comprising, as the active ingredient, creosote or phenolic derivatives constituting creosote. As having the activities to promote the absorption of intestinal juices and/or to retard the secretion of intestinal juices, the active ingredient lowers the intestinal juice level in intestines. As the phenolic derivatives, usable are one or more of guaiacol, creosol, phenol, cresol and xylenol. The regulator is especially effective for retarding the hypersecretion of intestinal juices to be caused by heat-labile or heat-stable enterotoxin of enterotoxigenic *Escherichia coli*.

5 Claims, 7 Drawing Sheets

INTESTINAL JUICE LEVEL REGULATOR

FIELD OF THE INVENTION

The present invention relates to an intestinal juice level regulator. More precisely, it relates to an intestinal juice level regulator, which comprises, as the active ingredient, creosote or phenolic derivatives constituting creosote, which promote the absorption of intestinal juices to thereby lower the intestinal juice level in the intestines.

BACKGROUND OF THE INVENTION

Heretofore, creosote has been used as an enterobactericide, as an antidiarrhetic based on its enterobactericidal activity, as an expectorant, as an antidiarrhetic based on its activity to retard intestinal movements, and also as an antispasmodic.

Creosote is described in "Medicine Production Guidelines" (edited by the Official Document Association of Japan), 1988, page 240, for the Standard for Approval of Commercial Production of Digestives, in which it is in the group of bactericides in Section No. 1 in Column V for antidiarrhetics. Creosote is also described in "Pathology" (written by H. Itoh; published by Keiko-do as the 6th revised edition on January 5, 1983), page 416, in which it is written that creosote is usable for enteric antisepsis and that, when administered through inhalation, it exhibits an expectorative activity. In the Pharmacopoeia of Japan, it is written that creosote can be used for expectoration, enteric hyperfermentation, cytotoxism, etc. In the United States Dispensatory, 27th Ed., 1973, page 355, it is written that creosote can be used as a bactericide for external application and as an expectorant for internal application. In "Pharmacology" ), Vol. 46, 1993, page 173, it is written by N. Ogata et al. that creosote exhibits an antidiarrhetic ability based on its activity to retard intestinal movements.

DISCLOSURE OF THE INVENTION

We, the present inventors, have studied to find unknown pharmaceutical activities of creosote which, as mentioned above, has heretofore being used as an enterobactericide, as an antidiarrhetic based on its enterobactericidal activity, as an expectorant, and as an antidiarrhetic based on its activity to retard intestinal movements. A a result, they have found that creosote has pharmaceutical activities to promote the absorption of intestinal juices and to retard the secretion thereof. Such pharmaceutical activities of creosote, which we have now found for the first time, could not be expected from the conventional knowledge of creosote. The present invention has been completed herein on the basis of this finding.

Specifically, the present invention provides an intestinal juice level regulator, which comprises, as the active ingredient, creosote or phenolic derivatives constituting creosote. Owing to the activities of the active ingredient to promote the absorption of intestinal juices and/or to retard the hypersecretion of intestinal juices, the intestinal juice level regulator of the invention lowers the intestinal juice level in intestines.

The phenolic derivatives include, for example, guaiacol, creosol, phenol, cresol and xylenol, and one or more of these are preferably used in the present invention.

The intestinal juice level regulator of the present invention is effective for curing various disorders in human beings and animals by retarding the hypersecretion of intestinal juices or promoting the absorption of intestinal juices, for example, for curing hypersensitive (large) intestinal syndromes, abdominal dysphoria, abdominal inflation, olighidria, trophopathy, intestinal juice malabsorption and hypersecretion owing to chemicals or poisons, etc. For example, the intestinal juice level regulator of the invention is effective in inhibiting the hypersecretion of intestinal juices caused by heat-labile or heat-stable enterotoxin of enterotoxigenic *Escherichia coli*.

DETAILED DESCRIPTION OF THE INVENTION

Figure 1:
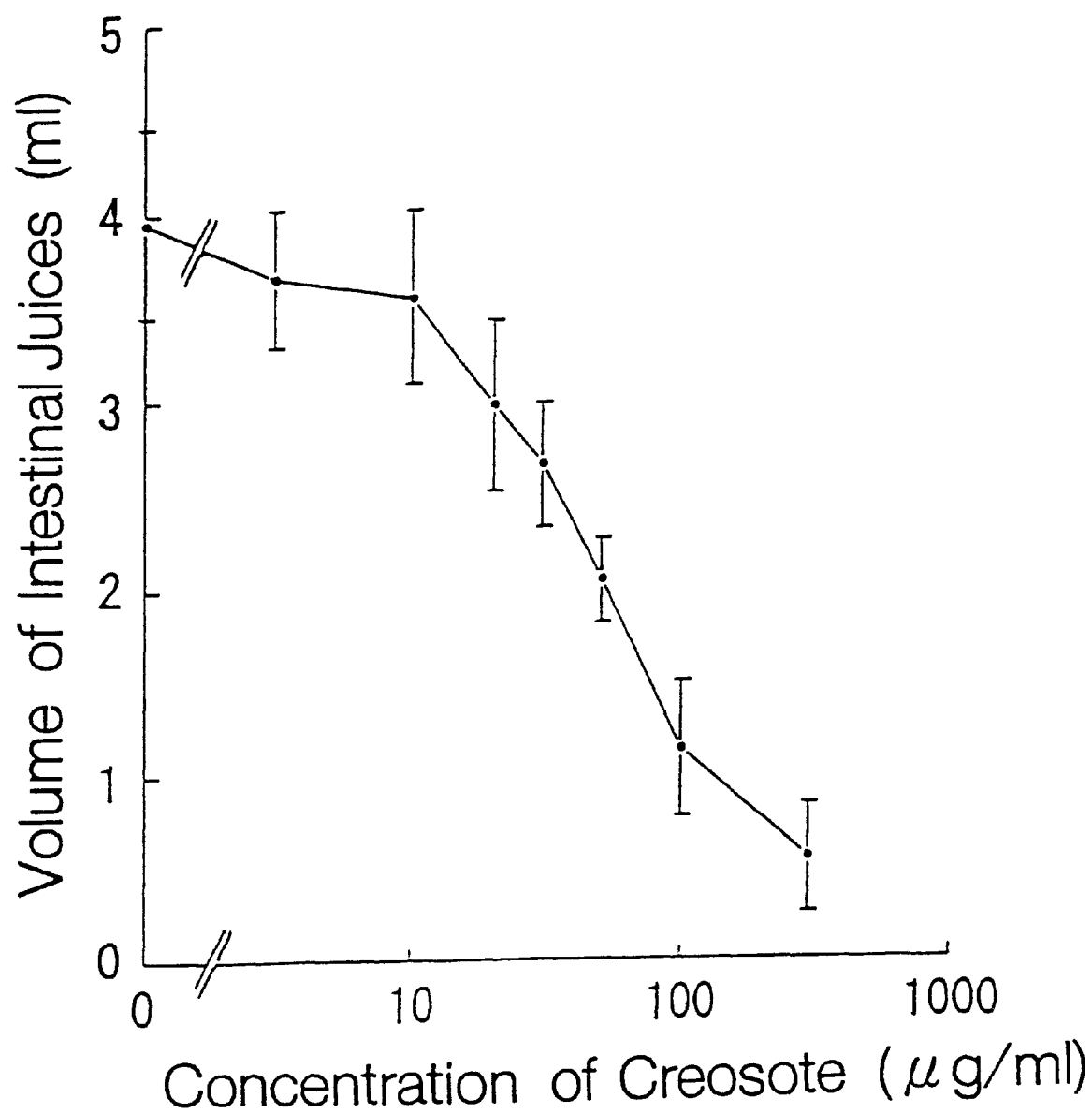
FIG. 1 is a graph showing the results of Pharmaceutical Experiment 1.

Creosote, which is the active ingredient in the pharmaceutical composition of the present invention, is itself known. For example, it is described in the Pharmacopoeia of Japan (13th Revision), the US National Formulary XII, etc. Creosote for use in the invention is a so-called wood creosote to be prepared through fractional distillation of wood tar as obtained from trees, especially broad-leaved trees such as beeches, oaks, maples, pines, etc., to collect the fraction as fractionated within the range of from 200 to 230° C. or so (at 760 mmHg); and this shall be distinctly differentiated from creosote obtained from petroleum tar (see N. Ogata and T. Baba, Res. Commun. Chem. Pathol. Pharmacol. 66, 411–423, 1989).

As in the above-mentioned references, creosote, which is the active ingredient in the pharmaceutical composition of the present invention, is a mixture comprising approximately from 20 to 35% of guaiacol, approximately from 15 to 25% of creosol, and other various phenolic derivatives such as phenols, cresols and xylenols. This is a colorless or pale yellow liquid having a characteristic smell of smoke and having a tongue-irritating taste, and has a specific gravity of 1.064 or larger.

In the intestinal juice level regulator of the present invention, creosote or phenolic derivatives constituting creosote, such as those mentioned hereinabove, are in any ordinary forms of general pharmaceutical formulations. For example, they may be formulated with any ordinary, pharmaceutically-acceptable vehicles and diluents in any ordinary manner to give various forms of preparations applicable to the intended therapeutical objects. Typical examples include oral preparations such as tablets, pills, powders, capsules, granules and liquids for internal use; intravascular preparations, intramuscular preparations, subcutaneous preparations and intracutaneous preparations such as injections; and rectal preparations such as suppositories.

To formulate the preparations of tablets, granules and powders, for example, various known carriers can be used, which include, for example, vehicles such as lactose, sucrose, glucose, starch and crystalline cellulose; binders such as hydroxypropyl cellulose, methyl cellulose, gelatin, tragacanth, arabic gum and sodium alginate; disintegrators such as starch, carboxymethyl cellulose and calcium carbonate; and lubricants such as magnesium stearate, talc and stearic acid. If desired, tablets may be coated with any ordinary coating materials to form sugar-coated tablets, film-coated tablets, etc. Also, if desired, tablets may be two-layered or multi-layered ones. In addition, granules and powders may also be coated with any ordinary coating materials.

To formulate the preparations of pills, employable are various carriers known in t he art, which include, for example, vehicles such as licorice powder, glucose and wheat flour; binders such as glycerin, aqueous syrup, arabic gum, tragacanth and gelatin; and disintegrators such as medicinal yeast, Aloe roots and Laminaria powder.

To formulate the preparations of capsules, employable are various carriers known in the art, which include, for example, vehicles such as lactose, olive oil and soybean oil.

The liquid preparations for internal use may be in any form of aqueous or oily suspensions, solutions, syrups and others. To formulate the liquid preparations, any ordinary additives are employable, including, for example, suspending agents such as sorbitol syrup, methyl cellulose, gelatin and carboxymethyl cellulose; and emulsifiers such as lecithin, sorbitan monooleate and arabic gum.

The injections may be in any form of suspensions, solutions, and emulsions in oily or aqueous vehicles. To formulate the injectable preparations, the composition of the invention may be mixed with any additives such as suspending agents, stabilizers and dispersants.

To formulate the preparations of suppositories, employable are any known carriers. For example, employable are bases such as cacao butter, glycerogelatin and macrogol. If desired, emulsifiers and suspending agents may be used for preparing the suppositories.

To the pharmaceutical composition of the invention, colorants and flavorings may be added too if desired.

The amount of the active ingredient, creosote or phenolic derivatives to be in the pharmaceutical composition of the present invention is not specifically defined, and may be suitably determined depending on the form of the composition. In general, however, the amount of the active ingredient in the composition is preferably from 0.2 to 60% or so relative to the total weight of the composition.

The dose of the intestinal juice level regulator of the present invention may be suitably determined, for example, depending on the sex, the age, the body weight and the condition of patients. In general, however, for oral and rectal administration to adults, the dose may be approximately from 1 to 500 mg/kg/day, preferably from 2 to 100 mg/kg/day or so, more preferably from 2 to 25 mg/kg/day or so, in terms of the active ingredient, creosote or phenolic derivatives constituting creosote. For injections for parenteral administration to adults, the dose may be approximately from 0.2 to 300 mg/kg/day, preferably from 0.2 to 50 mg/kg/day or so, more preferably from 0.5 to 5 mg/kg/day or so, in terms of the active ingredient, creosote or phenolic derivatives. The daily dose may be divided into 2 to 4 parts or so, which may be administered separately in one day.

Pharmaceutical Experiments with samples of the intestinal juice level regulator of the present invention are mentioned below.

Pharmaceutical Experiment 1
Test for the activity to promote the absorption of intestinal juices through intestinal walls:

Male, New Zealand White rabbits (Kbl NZW, 8-week aged) having a body weight of from 1.7 kg to 2.0 kg were fasted for 24 hours, and then anesthetized through intravenous injection of pentobarbital (from 25 to 30 mg/kg) into the otic vein. After having been shaven and disinfected, their abdomina were medisected, and the small intestine in each rabbit was ligated at the position of 10 cm from the top of the jejunum toward the anus. Next, starting from this position, the small intestine was further ligated at regular intervals of 5 cm toward the anus to produce 8 small intestinal sections in total. All the ligations were conducted without injuring the intestinal membranes and the blood vessels. Into each section, 6 ml of an artificial intestinal juice (10 mM sodium phosphate buffer (pH 7.2), 150 mM sodium chloride, 1 mg/ml bovine serum albumin, and 1% (v/v) methanol) containing 0, 3, 10, 20, 30, 50, 100 or 300$\mu$/ml of creosote was locally administered through a 10 ml-volume syringe provided with a 29-gauge needle. After the administration, the inside area of the abdomen was washed with 0.1% (w/v) pentcillin-containing physiological saline heated at 37° C., and the abdomen was closed through nodal suturation. Next, 6 hours after the administration, the rabbits were again anesthetized with pentobarbital, and their abdomina were sected. Then, the intestinal juice in each section was taken out through a syringe provided with a 23-gauge needle, and its volume was read from the gauge of the syringe. The data obtained are shown in FIG. 1. This data verifies the activity of creosote to promote the absorption of intestinal juices.

Figure 2:
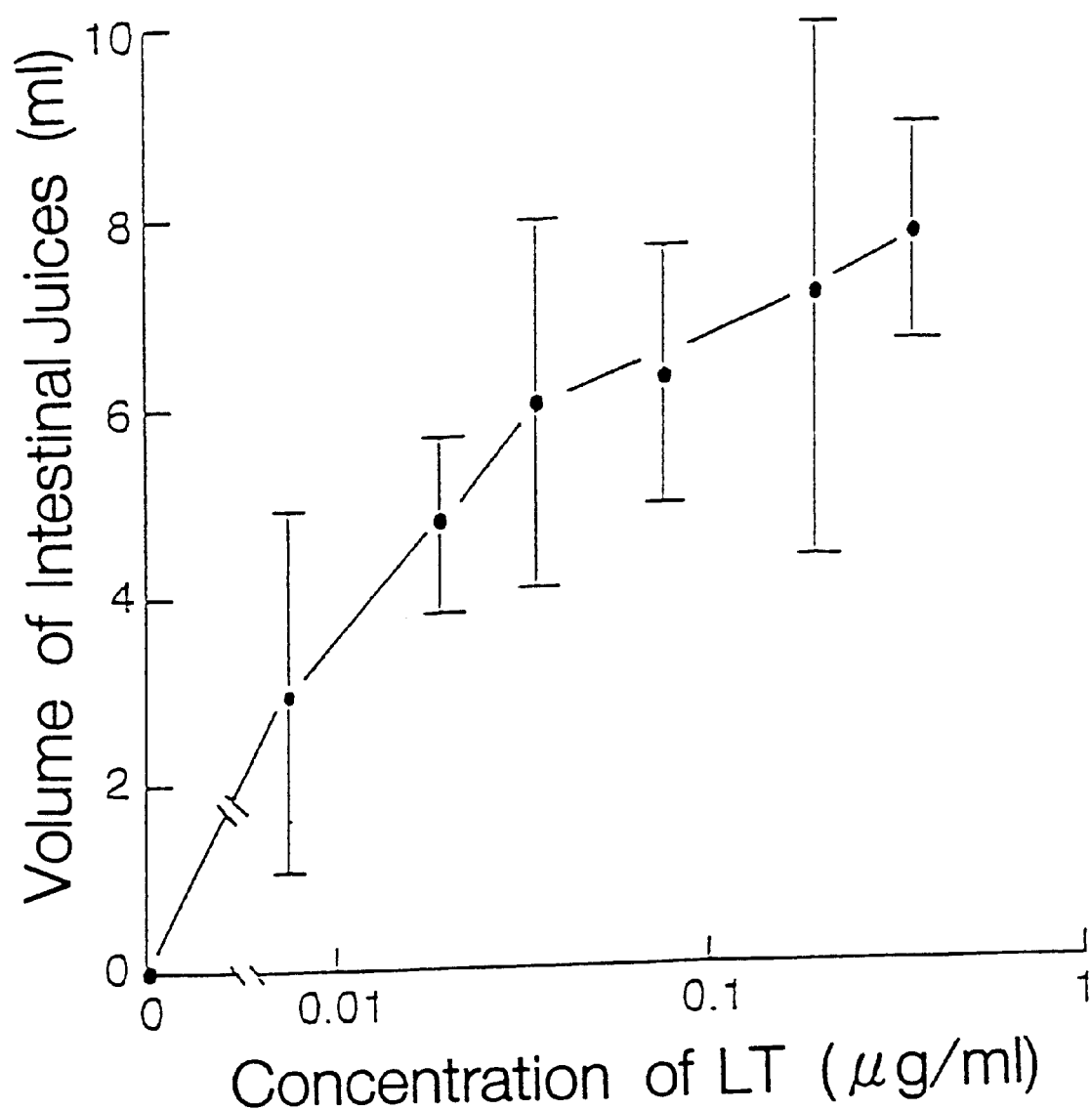
FIG. 2 is a graph showing the results of Pharmaceutical Experiment 2(a).

Pharmaceutical Experiment 2
Test for the activity to retard the hypersecretion of intestinal juices caused by heat-labile enterotoxin of enterotoxigenic *Escherichia coil* (LT):

(a) Male, New Zealand White rabbits (Kbl NZW, 8-week aged) having a body weight of from 1.7 kg to 2.0 kg were fasted for 24 hours, and then anesthetized through intravenous injection of pentobarbital (from 25 to 30 mg/kg) into the otic vein. After having been shaven and disinfected, their abdomina were medisected, and the small intestine in each rabbit was ligated at the position of 10 cm from the top of the jejunum toward the anus. Next, starting from this position, the small intestine was further ligated at regular intervals of 5 cm toward the anus to produce 8 small intestinal sections in total. All the ligations were conducted without injuring the intestinal membranes and the blood vessels. Into each section, 1.5 ml of an artificial intestinal juice (10 mM sodium phosphate buffer (pH 7.2), 150 mM sodium chloride, 1 mg/ml bovine serum albumin, and 1% (v/v) methanol) containing 0, 0.0067, 0.017, 0.033, 0.067, 0.17 or 0.33 $\mu$g/ml of LT was locally administered through a 10 ml-volume syringe provided with a 27-gauge needle. After the administration, the inside area of the abdomen was washed with 0.1% (w/v) pentcillin-containing physiological saline heated at 37° C., and the abdomen was closed through nodal suturation. Next, 18 hours after the administration, the rabbits were again anesthetized with pentobarbital, and their abdomina were sected. Then, the intestinal juice in each section was taken out through a syringe provided with a 23-gauge needle, and its volume was read from the gauge of the syringe. The data obtained are shown in FIG. 2. These verify the concentration-dependent activity of LT to promote the secretion of intestinal juices.

Figure 3:
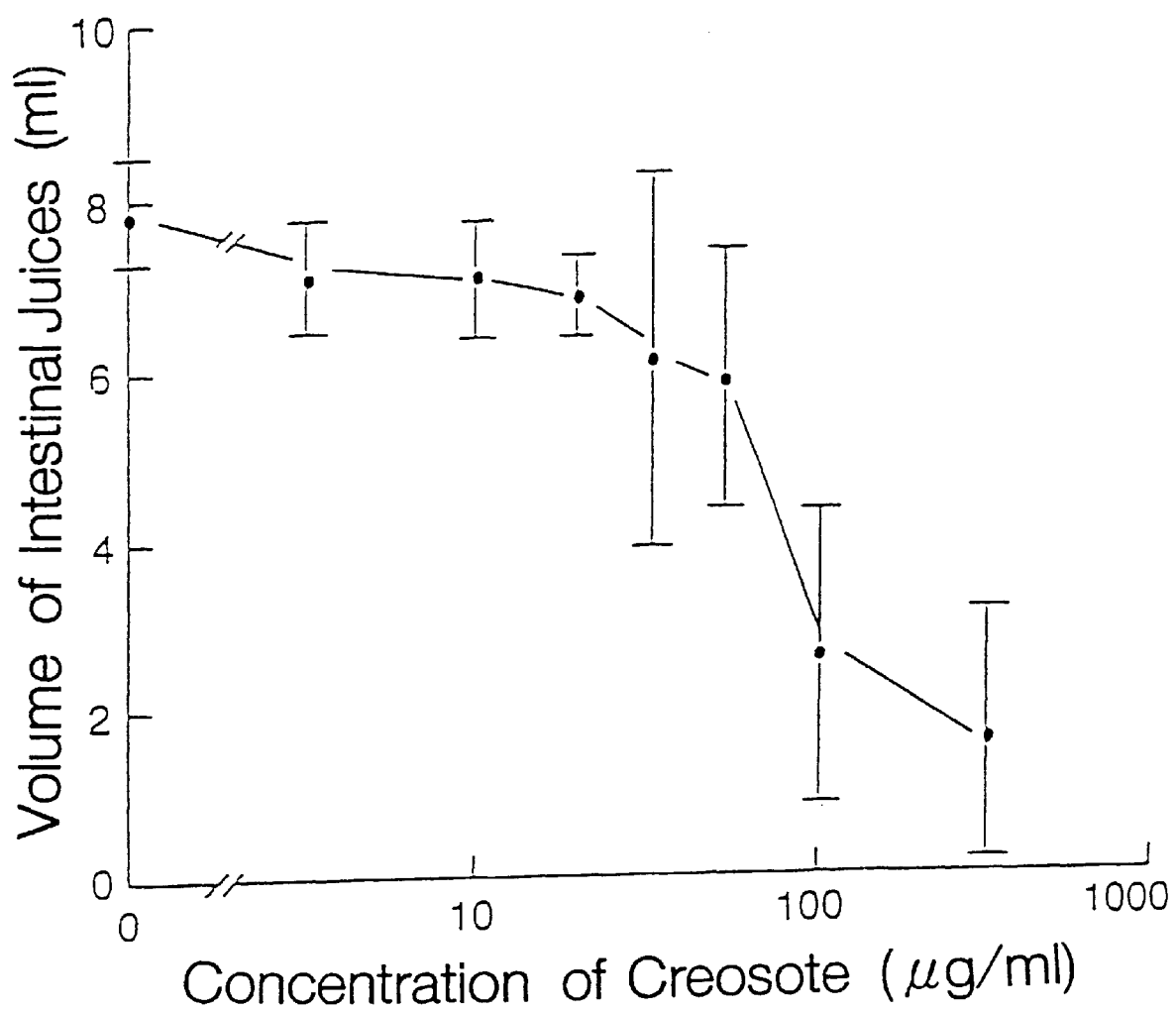
FIG. 3 is a graph showing the results of Pharmaceutical Experiment 2(b).

(b) Next, into each small intestinal section as formed in each rabbit in the same manner as above, locally administered was 1.5 ml of an artificial intestinal juice (10 mM sodium phosphate buffer (pH 7.2), 150 mM sodium chloride, 1 mg/ml bovine serum albumin, and 1% (v/v) methanol) containing 0, 3, 10, 20, 30, 50, 100 or 300 µg/ml of creosote and containing 0.033 µg/ml of LT, through a 10 ml-volume syringe provided with a 27-gauge needle. After the administration, the inside area of the abdomen was washed with 0.1% (w/v) pentcillin-containing physiological saline heated at 37° C., and the abdomen was closed through nodal suturation. Next, 18 hours after the administration, the rabbits were again anesthetized with pentobarbital, and their abdomina were sected. Then, the intestinal juice in each section was taken out through a syringe provided with a 23-gauge needle, and its volume was read from the gauge of the syringe. The data obtained are shown in FIG. 3. These verify the activity of creosote to retard the hypersecretion of intestinal juices as caused by LT.

Pharmaceutical Experiment 3

Figure 4:
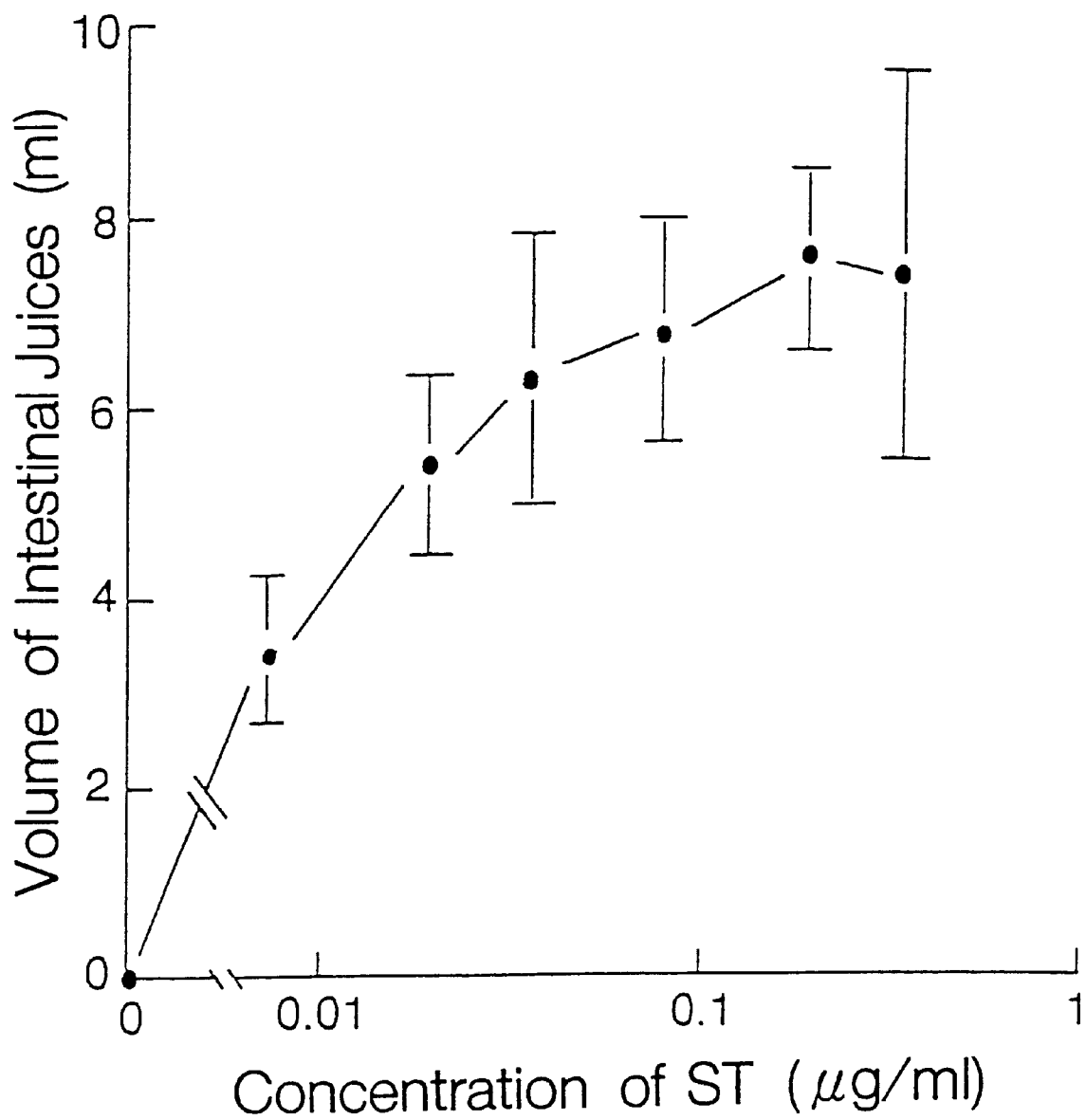
FIG. 4 is a graph showing the results of Pharmaceutical Experiment 3(a).

Test for the activity to retard the hypersecretion of intestinal juices caused by heat-stable enterotoxin of enterotoxigenic *Escherichia coli* (ST):

(a) Into each small intestinal section as formed in each rabbit in the same manner as in Pharmaceutical Experiment 2, 1.5 ml of an artificial intestinal juice (10 mM sodium phosphate buffer (pH 7.2), 150 mM sodium chloride, 1 mg/ml bovine serum albumin, and 1% (v/v) methanol) containing 0, 0.0067, 0.017, 0.033, 0.067, 0.17 or 0.33 µg/ml of LT was locally administered through a 2 ml-volume syringe provided with a 27-gauge needle. After the administration, the inside area of the abdomen was washed with 0.1% (w/v) pentcillin-containing physiological saline heated at 37° C., and the abdomen was closed through nodal suturation. Next, 18 hours after the administration, the rabbits were again anesthetized with pentobarbital, and their abdomina were sected. Then, the intestinal juice in each section was taken out through a syringe provided with a 23-gauge needle, and its volume was read from the gauge of the syringe. The data obtained are shown in FIG. 4. This data verifies the concentration-dependent activity of ST to promote the secretion of intestinal juices.

Figure 5:
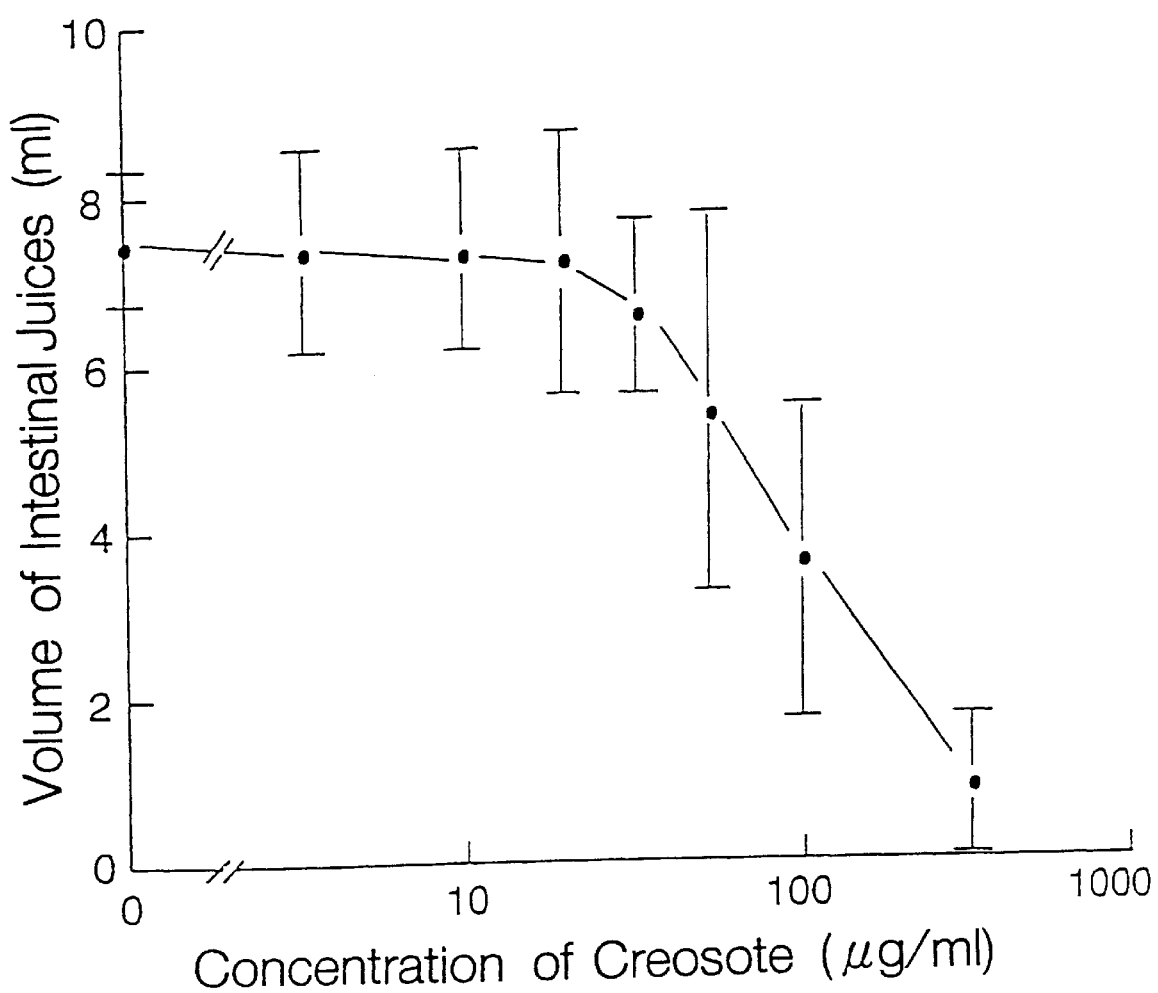
FIG. 5 is a graph showing the results of Pharmaceutical Experiment 3(b).

(b) Next, into each small intestinal section as formed in each rabbit in the same manner as above, 1.5 ml of an artificial intestinal juice (10 mM sodium phosphate buffer (pH 7.2), 150 mM sodium chloride, 1 mg/ml bovine serum albumin, and 1 % (v/v) methanol) containing 0, 3, 10, 20, 30, 50, 100 or 300 µg/ml of creosote and containing 0.033 µg/ml of ST was locally administered through a 10 ml-volume syringe provided with a 27-gauge needle. After the administration, the inside area of the abdomen was washed with 0.1% (w/v) pentcillin-containing physiological saline heated at 37° C., and the abdomen was closed through nodal suturation. Next, 18 hours after the administration, the rabbits were again anesthetized with pentobarbital, and their abdomina were sected. Then, the intestinal juice in each section was taken out through a syringe provided with a 23-gauge needle, and its volume was read from the gauge of the syringe. The data obtained are shown in FIG. 5. These verify the activity of creosote to retard the hypersecretion of intestinal juices as caused by ST.

Pharmaceutical Experiment 4

Influence of creosote on the activity of LT to promote the production of cyclic AMP (cAMP):

LT increases adenylate cyclase activity by ADP-ribosylation of α-subunit of G proteins in cell membranes and leads to elevation of cellular cAMP, which causes the hypersecretion of intestinal juices (see Mary Jacewicz, et al.; Textbook of Secretory Diarrhea, 139–162, 1990). Now, in order to clarify the mechanism of creosote in the above-mentioned Pharmaceutical Experiment 2, the influence of creosote on the promotion of cAMP production with LT was herein investigated.

Reactant solutions (80 µg of pigeon erythrocyte membranes, 100 µg/ml LT, 10 mM thymidine, 5 mM adenosine-5'-triphosphate (ATP), 1 mM nicotinamide adenine dinucleotide (NAD), 65% (v/v) of cytosol) each containing 0, 0.01, 0.1 or 1 mg/ml of creosote were heated at 37° C. for 30 minutes. The incubation was terminated by adding 1 ml of a cold solution A (10 mM Hepes buffer (pH 7.0), 130 mM sodium chloride, 0.1 mg/ul sodium azide). The membranes were recovered by centrifugation and suspended in 10 ml of 25 mM MOPS buffer (pH 7.5). Next, the resulting suspended was added to 25 mM MOPS buffer (pH 7.5) (12 mM creatinephosphoric acid, 5 U creatine dephosphorylase, 2 mM 2-mercaptoethanol, 6 mM magnesium chloride and 5 mM guanosine-5'-triphosphate (GTP)), heated at 37° C. for 40 minutes, and further heated in a boiling bath for 3 minutes. Next, after having been centrifuged, the resulting supernatant was diluted 10-fold with a buffer for an immunoassay. 50 µl of the resulting dilution was subjected to cAMP immunoassay (using a cAMP enzyme immunoassay kit, CAMP Immunoassay Kit produced by Cayman Chemical). The data obtained are shown in Table 1 below. These verify that creosote has no influence on the activity of LT to promote the production of cAMP and that the active point of creosote is limited to the stage after the production of cAMP. In other words, cAMP as once produced by LT acts directly or indirectly for promoting the secretion of intestinal juices, and it has been found that creosote works to retard the secretion of intestinal juices in any stage after the production of cAMP.

Figure 6:
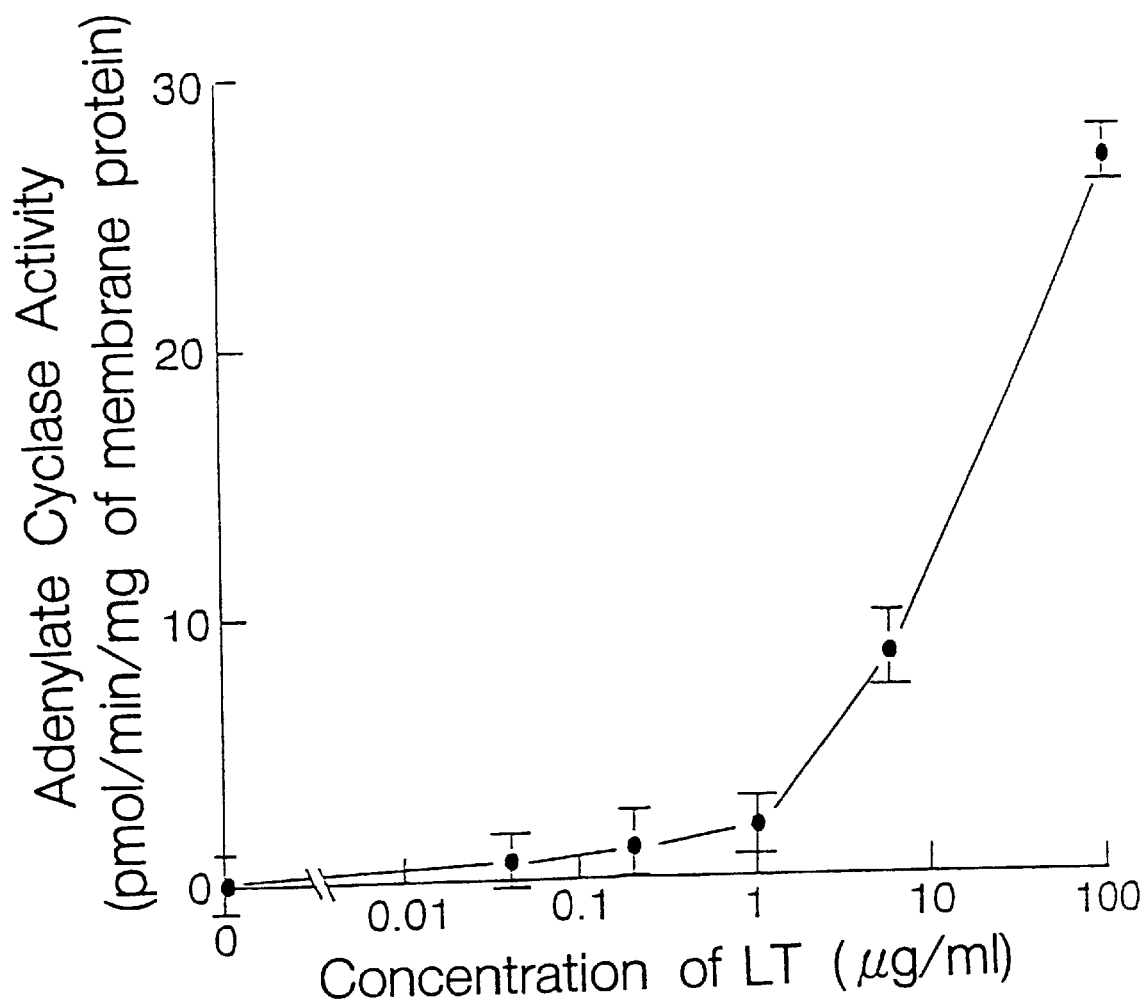
FIG. 6 is a graph relating to Pharmaceutical Experiment 4.

The LT concentration was settled to be 100 µg/ml in Pharmaceutical Experiment 4. This concentration was derived from the LT concentration-dependent test for the adenylate cyclase activation of LT, which had been carried out prior to the present experiment (see FIG. 6).

TABLE 1

Influence of Creosote on Adenylate Cyclase Activation of LT

| Concentration of Creosote (µg/ml) | Adenylate Cyclase Activity (pmol/min/mg of membrane protein) |
| --- | --- |
| 0 | 28.6 ± 1.8 |
| 1 | 23.1 ± 2.3 |
| 10 | 29.8 ± 2.4 |
| 100 | 27.6 ± 2.5 |

Pharmaceutical Experiment 5

Influence of cresote on the activity of ST to promote the production of cyclic GMP (cGMP):

ST activates guanylate cyclase in cell membranes and leads to elevation of cellular cGMP, which causes hypersecretion of intestinal juices (see Mary Jacewicz, et al.; Textbook of Secretory Diarrhea, 139–162, 1990). Now, in order to clarify the mechanism of creosote, the influence of creosote on the promotion of cGMP production with ST was herein investigated.

T84 cells (human colon cancer cells, American Type Culture Collection, CCL-248) as incubated in wells of a 24-well microtiter plate each filled with a mixed medium (1/1 mixture of Ham's F12 Medium and Dulbecco's Modified Eagle Medium), to a 100% confluent stage, were heated at 37° C. for 10 minutes in 0.5 ml of Dulbecco's Modified Eagle Medium containing 1 mM of isobutylmethylxanthine (IBMX). Next, a culture containing 0, 0.01, 0.1 or 1 mg/ml creosote and $10^{-7}$ M ST was added thereto, and heated at 37° C. for 30 minutes. The culture supernatant wa s removed, and 0.5 ml of cold, 0.1 M HCl was added to the residue. A part of the resulting solution was sampled and dried, to which was added 5 mM sodium acetate. Then, this was subjected to cGMP immunoassay (using a cGMP enzyme immunoassay kit, cGMP Immunoassay Kit produced by Cayman Chemical). The data obtained are shown in Table 2 below. This data verifies that creosote has no influence on the activity of ST to promote the production of cGMP and that the active point of creosote is limited to the stage after the production of cGMP. In other words, c GMP as once produced by ST acts directly or indirectly for promoting the secretion of intestinal juices, and it has been found that creosote works to retard the secretion of intestinal juices in any stage of the action of cGMP.

Figure 7:
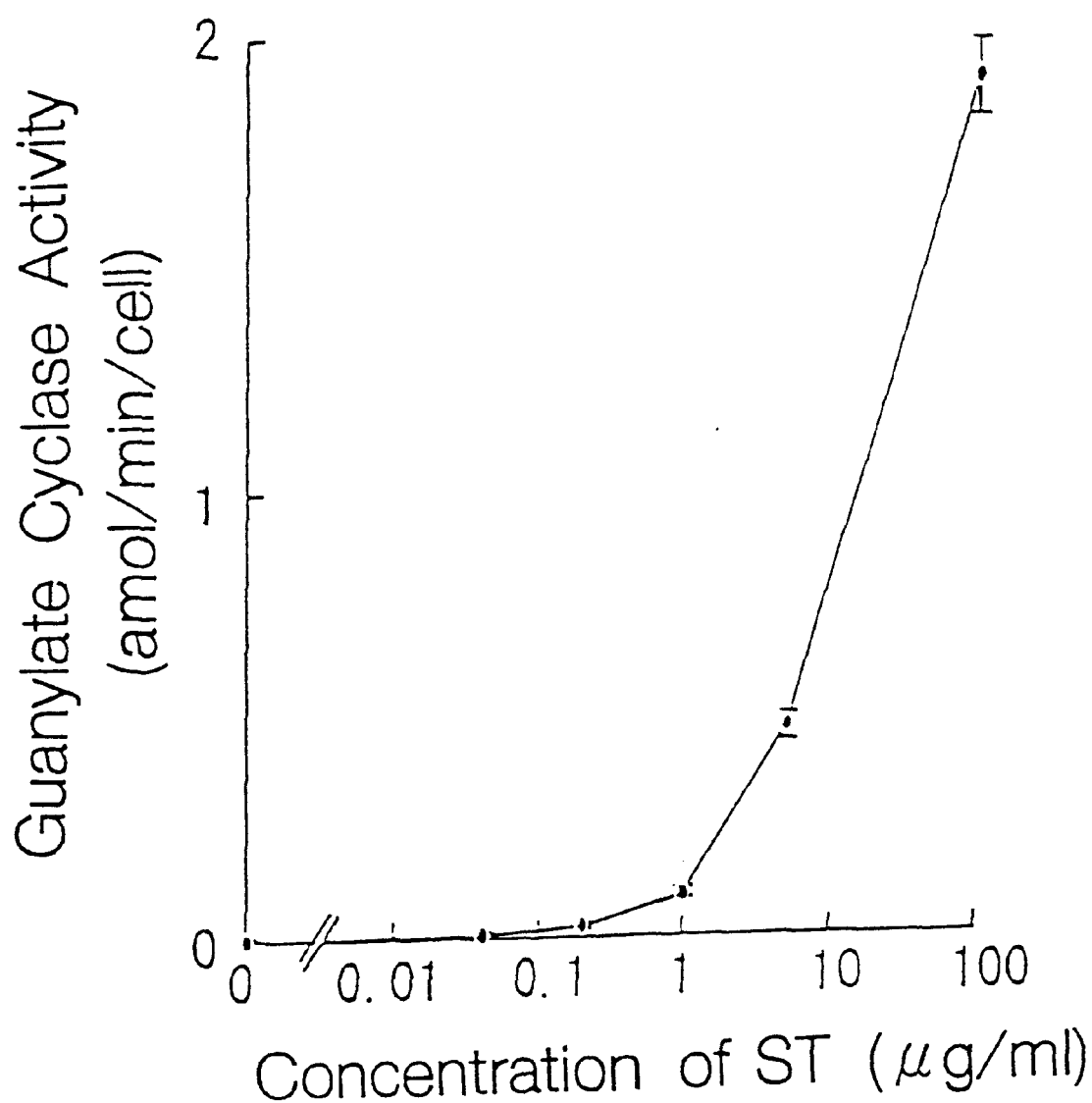
FIG. 7 is a graph relating to Pharmaceutical Experiment 5.

The ST concentration was settled to be $10^{-7}$ M in Pharmaceutical Experiment 5. This concentration was derived from the ST concentration-dependent test for the guanylate cyclase activation of ST, which had been carried out prior to the present experiment (see FIG. 7).

TABLE 2

Influence of Creosote on Guanylate Cyclase Activation of ST

| Concentration of Creosote ($\mu$g/ml) | Guanylate Cyclase Activity (amol/min/cell) |
| --- | --- |
| 0 | 1.6 ÷ 0.2 |
| 1 | 1.4 ± 0.3 |
| 10 | 1.8 ± 0.1 |
| 100 | 1.6 ± 0.2 |

The intestinal juice level regulator of the present invention may be put into practical use in various ordinary pharmaceutical preparations. Formulation Examples of the composition of the present invention are mentioned below, which, however, are not intended to restrict the scope of the invention.

FORMULATION EXAMPLE 1

Pills

| Component | Amount (mg) |
| --- | --- |
| Creosote | 50 |
| Licorice | 25 |
| Glycerin | 10 |
| Water | 50 |

The above-mentioned components were kneaded, the resulting blocks were pelletized with a pelletizer, and the resulting pellets were dressed into pills with a pill dresser. Thus were obtained pills having a creosote content of 50 mg/pill.

FORMULATION EXAMPLE 2

Capsules

| Component | Amount (mg) |
| --- | --- |
| Creosote | 100 |
| Starch | 250 |

Creosote and starch were mixed to give a powdery mixture, which was encapsulated into hard capsules having a creosote content of 100 mg/capsule.

FORMULATION EXAMPLE 3

Capsules

| Component | Amount (mg) |
| --- | --- |
| Creosote | 100 |
| Olive Oil | 200 |

Creosote was dissolved in olive oil to give a solution, which was encapsulated into soft capsules having a creosote content of 100 mg/capsule.

FORMULATION EXAMPLE 4

Tablets

| Component | Amount (mg) |
| --- | --- |
| Creosote | 150 |
| Lactose | 250 |
| Methyl Cellulose | 3 |
| Magnesium Stearate | 2 |
| Carboxymethyl Cellulose | 10 |

The above-mentioned components except magnesium stearate were mixed, and then kneaded with water to give granules. The resulting granules were dried, then mixed with magnesium stearate, and tabletted under compression. Alternatively, all the above-mentioned components were mixed and then directly tabletted under compression. Thus were obtained tablets each weighing 415 mg/tablet.

FORMULATION EXAMPLE 5

Injection

| Component | Amount (mg) |
| --- | --- |
| Creosote | 50 |
| Distilled Water for Injection | 2 |

50 mg of creosote was dissolved in distilled water for injection, put into a vial, sealed and sterilized to obtain an injection.

FORMULATION EXAMPLE 6

Pills

| Component | Amount (mg) |
| --- | --- |
| Guaiacol | 50 |
| Licorice | 25 |
| Glycerin | 10 |
| City Water | 50 |

The above-mentioned components were kneaded, the resulting blocks were pelletized with a pelletizer, and the resulting pellets were dressed into pills with a pill dresser. Thus were obtained pills having a guaiacol content of 50 mg/pill.

FORMULATION EXAMPLE 7
Capsules

| Component | Amount (mg) |
|---|---|
| Guaiacol | 50 |
| Cresol | 50 |
| Olive Oil | 100 |

Guaiacol and cresol were dissolved in olive oil in the ratio mentioned above, to give a solution, which was encapsulated into soft capsules having a guaiacol content of 50 mg/capsule and a cresol content of 50 mg/capsule.

FORMULATION EXAMPLE 8
Tablets

| Component | Amount (mg) |
|---|---|
| Creosol | 150 |
| Lactose | 250 |
| Methyl Cellulose | 3 |
| Magnesium Stearate | 2 |
| Carboxymethyl Cellulose | 10 |

The above-mentioned components except magnesium stearate were mixed, and then kneaded with water to give granules. The resulting granules were dried, then mixed with magnesium stearate, and tabletted under compression. Alternatively, all the above-mentioned components were mixed and then directly tabletted under compression. Thus were obtained tablets each weighing 415 mg/tablet.

While the invention has been described in detail and with reference to specific embodiments thereof, it will be apparent to one skilled in the art that various changes and modifications can be made therein without departing from the spirit and scope thereof.

What is claimed is:

1. The method of treating hypersensitive intestinal syndromes comprising administering to a patient in need thereof an intestinal juice regulator comprising, as an active ingredient, creosote or a phenolic derivative of creosote.

2. The method of treating abdominal dysphoria comprising administering to a patient in need thereof an intestinal juice regulator comprising, as an active ingredient, creosote or a phenolic derivative of creosote.

3. The method of treating abdominal inflation comprising administering to a patient in need thereof an intestinal juice regulator comprising, as an active ingredient, creosote or a phenolic derivative of creosote.

4. The method of treating olighidria comprising administering to a patient in need thereof an intestinal juice regulator comprising, as an active ingredient, creosote or a phenolic derivative of creosote.

5. The method of treating trophopathy comprising administering to a patient in need thereof an intestinal juice regulator comprising, as an active ingredient, creosote or a phenolic derivative of creosote.

* * * * *